United States Patent [19]

Cornils et al.

[11] Patent Number: 4,808,757

[45] Date of Patent: Feb. 28, 1989

[54] PROCESS FOR THE PREPARATION OF ALDEHYDES

[75] Inventors: Boy Cornils, Hofheim; Werner Konkol, Oberhausen; Hanswilhelm Bach; Wilhelm Gick, both of Duisburg; Ernst Wiebus, Oberhausen; Helmut Bahrmann, Hamminkeln-Brunen; Heinz-Dieter Hahn, Oberhausen, all of Fed. Rep. of Germany

[73] Assignee: Ruhrchemie Aktiengesellschaft, Fed. Rep. of Germany

[21] Appl. No.: 193,956

[22] Filed: May 13, 1988

Related U.S. Application Data

[63] Continuation of Ser. No. 944,427, Dec. 19, 1986, abandoned.

[30] Foreign Application Priority Data

Dec. 24, 1985 [DE] Fed. Rep. of Germany ....... 3546123

[51] Int. Cl.$^4$ .............................................. C07C 45/50
[52] U.S. Cl. .................................... 568/454; 568/458
[58] Field of Search ........................ 568/454, 451, 458

[56] References Cited

U.S. PATENT DOCUMENTS

| | | | |
|---|---|---|---|
| 4,248,802 | 2/1981 | Kuntz et al. | 568/454 |
| 4,299,990 | 11/1981 | Tummes et al. | 568/454 |
| 4,399,312 | 9/1983 | Russel et al. | 568/454 |
| 4,533,757 | 9/1985 | Kummer et al. | 568/454 |
| 4,577,043 | 3/1986 | Kalbfell et al. | 568/454 |
| 4,578,523 | 3/1986 | Bahrmann et al. | 568/454 |
| 4,593,126 | 6/1986 | Cornils et al. | 568/454 |

*Primary Examiner*—Warren B. Lone
*Attorney, Agent, or Firm*—Bierman & Muserlian

[57] ABSTRACT

A process for the preparation of aldehydes by hydroformylation of olefins in the presence of an aqueous solution containing rhodium as a catalyst. The aqueous solution preferably contains rhodium in a concentration of 450 to 800 weight-ppm and sulfonated or carboxylated triarylphosphines as complex ligands in a concentration of 25 to 30% by weight, both based on the aqueous solution.

16 Claims, No Drawings

PROCESS FOR THE PREPARATION OF ALDEHYDES

PRIOR APPLICATION

This application is a continuation of U.S. patent application Ser. No. 944,427 filed Dec. 19, 1986, now abandoned.

The present invention relates to a process for the preparation of aldehydes by the hydroformylation of olefins in the presence of water-soluble rhodium complex compounds as catalysts.

The preparation of aldehydes and alcohols by the reaction of olefins with carbon monoxide and hydrogen is known. The reaction is catalyzed with hydridocarbonyls, preferably those of the metals of the 8th Group of the Periodic Table. In place of cobalt, which finds widespread commercial application as a catalyst metal, rhodium has also been gaining significance in the past few years. In contrast to cobalt, rhodium permits the reaction to be carried out at low pressure. Moreover, straight-chain n-aldehydes are formed preferably, with only a minor amount of iso-aldehydes. Finally, with the use of rhodium catalysts, the hydrogenation of olefins to saturated hydrocarbons is also much less than with the use of cobalt catalysts.

With the commercially established processes, the rhodium catalyst is used in the form of modified hydridorhodium carbonyls which contain additional and, in some cases, excess ligands. Tertiary organic phosphines or esters of phosphoric acid have proved particularly useful as ligands. Their application makes it possible to reduce the reaction pressure to under 30 MPa.

However, with this process, the separation of the reaction products and the recovery of the catalysts homogeneously dissolved in the reaction product cause problems. Generally, the reaction product is distilled out of the reaction mixture. In practice, however, this route can only be employed for the hydroformylation of lower olefins; i.e. olefins with up to 5 carbon atoms in the molecule, owing to the thermal sensitivity of the aldehydes and alcohols formed. Furthermore, it has become apparent that the thermal loading of the distillate also leads to considerable catalyst losses owing to the decomposition of the rhodium complex compounds.

The disadvantages described are avoided by the use of catalyst systems which are soluble in water. Such catalysts are described, for example, in DE-PS No. 26 27 354. Solubility of the rhodium complex compounds in water is achieved by the use of sulfonated triarylphosphines as complex ligands. With this variation on the process, the catalyst can be separated from the reaction product after completion of the hydroformylation reaction simply by separating of the aqueous and organic phases; i.e. without distillation and therefore without any additional thermal process steps. Apart from sulfonated triarylphosphines, carboxylated triarylphosphines are also used as complex components of the water-soluble rhodium complex compounds.

The olefin is reacted with carbon monoxide and hydrogen in an aqueous phase which contains the catalyst. The rhodium concentration in this phase is usually 50 to 800 ppm, based on the aqueous solution.

A measurement of the effectiveness of the catalyst system consisting of rhodium and water-soluble ligand is the number of mols of aldehyde which are formed per unit volume of catalyst solution and per unit time. In the following formula, the term "productivity" is used to describe this relationship; i.e.

$$\text{productivity} = \frac{\text{mols aldehyde}}{\text{l catalyst solution} \times h}$$

The productivity increases as the amount of rhodium in the aqueous catalyst solution increases. Moreover, the rhodium concentration influences the stability of the sulfonated or carboxylated triarylphosphines; as the rhodium concentration increases, the tendency of the phosphorus/carbon bond to split forming, for example, substituted phosphinic acid derivatives and aryl sulfonates or aryl carboxylates, also increases. This reaction finally leads to a decrease in the activity of the catalyst system.

The rhodium complex compound contains a maximum of three phosphine molecules per rhodium atom. However, it is recommended that a large excess of phosphine based on the rhodium present be used to increase its stability. Therefore, it is customary to use 10 to 100 mols, preferably 50 to 100 mols water-soluble phosphine per gram-atom of rhodium. A high phosphine excess is also desirable because, during the course of the hydroformylation reaction, P(III) and P(V) compounds are formed irreversibly, particularly through hydrolysis and/or oxidation. These compounds are no longer capable of forming complexes with rhodium.

Furthermore, the industry requires that a catalyst have long life under its typical working conditions, even under full load. The period between the insertion of the catalyst and its replacement with fresh catalyst owing to intolerable loss of activity should be as long as possible.

Therefore, the problem consisted of the need to develop a process for the preparation of aldehydes by the reaction of aliphatic olefins with 2 to 12 carbon atoms with carbon monoxide and hydrogen. The reaction should take place in the liquid phase in the presence of water and rhodium (in metallic form or as a compound) and the water-soluble salt of a sulfonated or carboxylated triarylphosphine should combine high productivity of the catalyst solution with long life of the catalyst system.

This problem is solved by a process of the aforementioned type wherein the rhodium concentration in the aqueous phase is 450 to 800 weight-ppm and the concentration of the sulfonated or carboxylated triarylphosphines is 25 to 30% by weight, based on the aqueous solution. It has proved particularly successful to maintain the concentration of the sulfonated or carboxylated triarylphosphines at 26 to 28% by weight, based on the aqueous solution. It has been shown that careful coordination of the rhodium concentration and the concentration of the sulfonated or carboxylated phosphines ensures both high productivity of the catalyst solution and long life of the catalyst system.

Furthermore, it has been determined that the productivity of the catalyst system depends not only on the rhodium concentration, but also on the concentration of the sulfonated or carboxylated triarylphosphines in the catalyst solution. While an increase in the phosphine concentration increases the catalyst's life, it also leads to a decline in the rate of the hydroformylation reaction and thus to a reduction in productivity of the catalyst system.

In the process of the present invention, it is possible to hydroformylate olefins with 2 to 12 carbon atoms.

These olefins can be linear or branched, with internal or terminal double bonds. Examples of such olefins are: ethylene, propylene, 1-butene, 2-butene, 1-pentene, 2-methyl-1-butene, 4,4-dimethyl-1-nonene, and 1-dodecene. Linear olefins with 2 to 8 carbon atoms such as ethylene, propylene, 1-butene, 1-pentene, 1-hexene, 1-heptene, and 1-octene are preferably employed.

Rhodium or rhodium compounds are used as catalysts together with water-soluble phosphines which have the general formula:

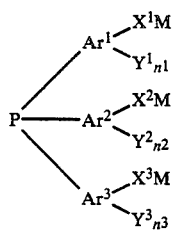

In this formula $Ar^1$, $Ar^2$, and $Ar^3$ each denote a phenyl or naphthyl group; $Y^1$, $Y^2$, and $Y^3$ each represent a straight-chain or branched alkyl group with 1 to 4 carbon atoms, an alkoxy group, a halogen atom; OH, CN, $NO_2$, or $R^1R^2N$ groups where $R^1$ and $R^2$ each stand for a straight-chain or branched alkyl group with 1 to 4 carbon atoms; $X^1$, $X^2$, and $X^3$ are each a sulfonate ($SO_3^-$) group or a carboxylate ($COO^-$) group; $n^1$, $n^2$, and $n^3$ are the same or different whole numbers from 0 to 5; M is an alkali metal ion, the equivalent of an alkaline earth metal or zinc ion, an ammonium ion, or a quaternary alkylammonium ion of the general formula $N(R^3R^4R^5R^6)^+$, wherein $R^3$, $R^4$, $R^5$, and $R^6$ each denote a straight-chain or branched alkyl group, in particular one having 1 to 4 carbon atoms.

According to a preferred embodiment of this process, compounds of the general formula described above are used as water-soluble phosphines where $Ar^1$, $Ar^2$, and $Ar^3$ are each a phenyl group and $X^1$, $X^2$, and $X^3$ are each a sulfonate group or a carboxylate group. Examples of compounds with the general formula described above are triphenylphosphine trisodium trisulfonate, triphenylphosphine tri(tetraalkylammonium)trisulfonate, triphenylphosphine trisodium tricarboxylate.

The sulfonated or carboxylated aryl phosphines can be employed as single compounds. However, phosphine mixtures containing different numbers of sulfonic acid groups or carboxylate groups can also be used; for example, mixtures of triarylphosphine trisulfonic acids and triarylphosphine disulfonic acids. Moreover, the sulfonates or carboxylates need not contain the same cation. Mixtures of salts derived from different metals and/or containing ammonium and/or quaternary alkylammonium ions are suitable.

The rhodium is used either in metallic form or as a compound. If metallic rhodium is used, it is preferably applied to a carrier such as activated carbon, calcium carbonate, aluminium silicate, or alumina. The substances which can be considered as rhodium compounds are water-soluble or water-soluble under the reaction conditions. Suitable compounds include the various rhodium oxides, salts of inorganic hydrogen and oxygen acids, as well as salts of aliphatic mono- and polycarboxylic acids. As examples, rhodium chloride, rhodium nitrate, rhodium sulfate, rhodium acetate, and rhodium malonate, are all useful. Furthermore, rhodium carbonyl compounds such as tricarbonyl rhodium, tetracarbonyl rhodium, and complex salts of rhodium, e.g. cyclooctadienyl rhodium chloride can be used; however, rhodium oxide, rhodium chloride, and rhodium acetate are preferred. Under the reaction conditions, rhodium complex compounds containing carbon monoxide and phosphines as ligands are formed both from metallic rhodium and from rhodium compounds, the rhodium complex compounds forming the catalyst system together with the excess phosphines.

The catalyst solution can be prepared in advance; e.g. from the aqueous phosphine solution and the required amount of rhodium, and then introduced into the reaction zone. However, it is equally possible to prepare the catalyst solution by mixing the components in the reaction zone itself. The rhodium is present in the aqueous catalyst solution in a concentration of 450 to 800 weight-ppm, preferably 500 to 600 weight-ppm, based on the solution.

The total pressure of the hydrogen and carbon monoxide is 1 to 200 bar (100 to $2\times 10^4$ kPa), preferably 10 to 100 bar ($1\times 10^3$ to $1\times 10^4$ kPa). The composition of the synthesis gas; i.e. the ratio of carbon monoxide to hydrogen, can be varied within wide limits. Generally, synthesis gas is used where the volume ratio of carbon monoxide to hydrogen is 1 : 1 or only deviates slightly from this value. The reaction takes place at temperatures of 20 to 150° C. and can be carried out either continuously or batchwise.

The following examples are intended to illustrate the invention:

EXAMPLE 1

Propylene, carbon monoxide and hydrogen in a volume ratio of 1 : 1 : 1 are introduced into an aqueous catalyst colution containing 27% by weight of a mixture of the sodium salts of triphenylphosphine trisulfonic acid and triphenylphosphine disulfonic acid along with 500 ppm rhodium while stirring at a temperature of 122° C. and a pressure of 5.0MPa. Per catalyst solution and per hour, 1,95 mols of a mixture of n and iso-butyraldehydes are obtained, the n/iso-ratio being 95 : 5.

EXAMPLE 2

Example 1 is repeated, except that the catalyst solution cintained 30% by weight of a mixture of sodium salts of triphenylphosphine trisulfonic acid and triphenylphosphine disulfonic acid, the rhodium concentration being unchanged. Per catalyst solution and per hour, 1.7 mols of a mixture of n and iso-butyraldehyde are formed, the n/iso-ratio being 94 : 6

EXAMPLE 3

Example 1 is repeated, except that the catalyst slution contains 14.5% by weight of a mixture of sodium salts of triphenylphosphine trisulfonic acid and triphenyl disulfonic acid, the rhodium concentration being unchanged. Per catalyst solution and per hour, 3.1 mols of a mixture of n and isobutyraldehyde are formed. However, under the aforementioned reaction conditions, a large amount of the P(III) compounds change to P(V) compounds, so that the catalyst solution loses its activity after only a brief use. The phosphine concentration selected is therefore unsuitable for economic application.

What we claim is:

1. A process for the preparation of aldehydes by the reaction of aliphatic olefins having 2 to 12 carbon atoms with carbon monoxide and hydrogen in the liquid phase in the presence of water, rhodium, and at least one water-soluble salt of a sulfonated or carboxylated triarylphosphine, wherein the concentration of said rhodium in the aqueous phase is 450 to 800 weight-ppm and the concentration of said triarylphosphines is 25 to 30% by weight, in each case based on the aqueous solution.

2. The process of claim 1 wherein said rhodium is a metallic form.

3. The process of claim 1 wherein said rhodium is present as a compound.

4. The process of claim 1 wherein said concentration is 26% to 28% by weight based on said aqueous solution.

5. The process of claim 2 wherein said concentration is 26% to 28% by weight based on said aqueous solution.

6. The process of claim 3 wherein said concentration is 26% to 28% by weight based on said aqueous solution.

7. The process of claim 1 wherein said rhodium is present in said aqueoous solution in a concentration of 500 to 600 weight-ppm, based on said aqueous solution.

8. The process of claim 2 wherein said rhodium is present in said aqueous solution in a concentration of 500 to 600 weight-ppm, based on said aqueous solution.

9. The process of claim 3 wherein said rhodium is present in said aqueous solution in a concentration of 500 to 600 weight-ppm, based on said aqueous solution.

10. The process of claim 4 wherein said rhodium is present in said aqueous solution in a concentration of 500 to 600 weight-ppm, based on said aqueous solution.

11. The process of claim 5 wherein said rhodium is present in said aqueous solution in a concentration of 500 to 600 weight-ppm, based on said aqueous solution.

12. The process of claim 6 wherein said rhodium is present in said aqueous solution in a concentration of 500 to 600 weight-ppm, based on said aqueous solution.

13. The process of claim 1 wherein said triarylphosphine is of the formula

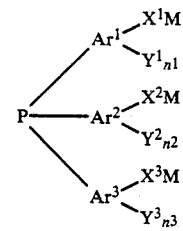

wherein $Ar^1$, $Ar^2$, and $Ar^3$ are individually phenyl or napthyl; $Y^1 Y^2$, and $Y^3$ are individually a straight-chain or branched alkyl group having 1 to 4 carbon atoms, an alkoxyl group, a halogen atom, OH, CN, $NO_2$, or $R^1R^2N$ groups wherein $R^1$ and $R^2$ are individually a straight-chain or branched alkyl group having 1 to 4 carbon atoms; $X^1$, $X^2$, and $X^3$ are individually sulfonate or carboxylate; $n^1$, $n^2$, and $n^3$ are individually a whole number from 0 to 5; M is an alkali metal ion, the equivalent of an alkaline earth metal or zinc ion, an ammonium ion, or a quaternery alklylammonium ion of the formula $N(R^3R^4R^5R^6)+$, wherein $R^3$, $R^4$, $R^5$, and $R^6$ are individually a straight-chain or branched alkyl.

14. The process of claim 13 wherein $R^3$, $R^4$, $R^5$, and $R^6$ are individually an alkyl having 1 to 4 carbon atoms.

15. The process of claim 13 wherein $Ar^1$, $Ar^2$, and $Ar^3$ are phenyl and $X^1$, $X^2$, and $X^3$ are individually sulfonate or carboxylate.

16. The process of claim 13 wherein said triarylphosphine is taken from the class consisting of triphenylphosphine trisodium trisulfonate, triphenylphosphine tri(tetraalkylammonium) trisulfonate, triphenylphosphine trisodium tricarboxylate, and mixtures thereof.

* * * * *